United States Patent

Pollack et al.

[11] Patent Number: 6,146,326
[45] Date of Patent: Nov. 14, 2000

[54] ENDOSCOPE

[76] Inventors: Michael J. Pollack, 2089 N. Line St., Lansdale, Pa. 19446; Guy M. Atkinson, 429 Ridge Rd., Telford, Pa. 18969; Eugene J. Kelly, 4 Leeward Cove, Bayville, N.Y. 11709

[21] Appl. No.: 08/995,063

[22] Filed: Dec. 19, 1997

Related U.S. Application Data

[62] Division of application No. 08/773,894, Jan. 31, 1996.

[51] Int. Cl.⁷ .................................................. G02B 23/24
[52] U.S. Cl. .......................... 600/141; 600/160; 600/176; 600/182; 600/133
[58] Field of Search .................................... 600/129, 130, 600/128, 133, 139, 141, 142, 144, 160, 176, 182; 359/439, 435

[56] References Cited

U.S. PATENT DOCUMENTS

| | | | |
|---|---|---|---|
| 4,148,550 | 4/1979 | MacNally | 350/54 |
| 4,341,205 | 7/1982 | Hosano . | |
| 4,798,452 | 1/1989 | Erb . | |
| 4,834,497 | 5/1989 | Angel . | |
| 4,988,163 | 1/1991 | Cohen . | |
| 5,061,026 | 10/1991 | Clarke . | |
| 5,097,359 | 3/1992 | McKinley | 600/176 |
| 5,182,791 | 1/1993 | Pollack . | |
| 5,210,814 | 5/1993 | McNally | 600/138 |
| 5,349,941 | 9/1994 | Hori . | |
| 5,369,525 | 11/1994 | Bala | 359/435 |
| 5,411,020 | 5/1995 | Ito . | |
| 5,416,634 | 5/1995 | Ning | 359/435 |
| 5,463,712 | 10/1995 | Cawood | 600/160 |
| 5,536,244 | 7/1996 | Muller | 600/133 |
| 5,554,099 | 9/1996 | Cawood | 600/160 |

*Primary Examiner*—Gene Mancene
*Assistant Examiner*—Ira Hatton
*Attorney, Agent, or Firm*—Ratner & Prestia

[57] ABSTRACT

An endoscope contains no adhesives, epoxies, or other organic materials. The endoscope includes a set of lenses held in position by cylindrical spacers. A pair of windows seal the ends of the endoscope, and prevent the lenses and spacers from falling out. The windows are brazed to the endoscope. Due to the use of brazing, no adhesives are needed to hold the lenses or windows in place. Thus, one can sterilize the endoscope in the high temperature environment of an autoclave, without risking damage to the optical components. The brazing produces a hermetic seal which enables the endoscope to function properly in an environment of high temperature or high pressure, or in chemically abusive environments.

7 Claims, 4 Drawing Sheets

ENDOSCOPE

This is a division of application Ser. No. 08/773,894, filed Jan. 31, 1966.

BACKGROUND OF THE INVENTION

The present invention relates to endoscopes, and, in particular, provides an endoscope that can be safely sterilized in an autoclave.

Endoscopes typically include a plurality of concentric tubes which define passages for a set of lenses and for bundles of optical fibers. The optical fibers carry light which illuminates the lenses and allows the user to view a desired part of the body. One or both ends of the endoscope may include windows, although one of the lenses can comprise a window. The windows provide a hermetic seal against the outside environment The tubes defining the endoscope are usually rigid, and can be made of stainless steel.

In the prior art, it has been known to use adhesives to mount the lenses and/or the windows to the tube. Epoxies or other organic materials are commonly used to hold the lenses in place within the endoscope, to attach the windows to the ends of the tube, and/or to hold the optical fibers in position. But epoxies and other adhesives have the disadvantage that they deteriorate when exposed to heat and steam.

An autoclave is the preferred device for sterilizing an endoscope. But an autoclave generally produces temperatures in the range of about 270° F. After repeated exposure to the heat of an autoclave, the epoxy seals tend to deteriorate and fail. A mismatch in the coefficient of expansion between the endoscope wall and the lenses and windows can cause the endoscope tube to rip away from the epoxy. Optical fibers held in place by epoxy may become loose or even break due to deterioration of the epoxy. As a result, what is intended to be a hermetic seal becomes less than hermetic.

Epoxies and other adhesives also evaporate when subjected to heat. When one heats and then cools a conventional endoscope, the evaporated material will condense on the lenses, forming a film which becomes thicker after repeated cycles of heating and cooling. Thus, an additional disadvantage of a conventional endoscope is that, after repeated autoclaving cycles, the optical transmissivity of its lenses decreases so much that the endoscope must be replaced.

The present invention provides an endoscope which has no adhesives or epoxies whatever. By avoiding such materials, one can build an endoscope which suffers no harm in an autoclave, even after repeated thermal stress.

SUMMARY OF THE INVENTION

The endoscope of the present invention includes inner and outer tubes, and a plurality of lenses located inside the inner tube. At least one bundle of optical fibers extends along the length of the tubes, between the inner and outer tubes. The distal and proximal ends of the endoscope have windows, preferably made of sapphire. The windows are affixed to the tubes by brazing. According to the invention, the sapphire is first coated with a layer of metal, and the metal layer is then coated with a brazing material. The brazing material, which may be nickel, is bonded to at least one of the tubes. Thus, the windows are affixed to the endoscope without the use of epoxies or other adhesives.

The lenses are held in place, within the inner tube, by a plurality of spacers which comprise cylinders arranged between pairs of lenses. Again, there are no epoxies or other adhesives holding the lenses. In a preferred embodiment, the spacers include slots, which permit the spacers to bend or buckle slightly, to accommodate thermal stress without damaging or destroying the endoscope.

Due to the brazing of the windows to the tube, and due to the use of spacers to hold the lenses in place, the endoscope of the present invention does not need adhesives. The endoscope can therefore withstand the high temperatures generated in an autoclave, without showing any deterioration, even after repeated autoclaving cycles.

The present invention therefore has the primary object of providing an endoscope which can be sterilized in an autoclave without deteriorating.

The invention has the further object of providing an endoscope which has no adhesives or epoxies, or the like, so that the endoscope can withstand high temperatures without undesirable effects.

The invention has the further object of improving the reliability and useful life of endoscopes.

The invention has the further object of providing an endoscope which is readily sterilizable in an autoclave.

The invention has the further object of prolonging the useful life of the lenses of an endoscope.

The invention has the further object of reducing the tendency of the lenses in an endoscope to tilt or chip when the endoscope is heated or cooled.

The invention has the further object of providing a method of making an endoscope.

The reader skilled in the art will recognize other objects and advantages of the present invention, from a reading of the following brief description of the drawings, the detailed description of the invention, and the appended claims.

DETAILED DESCRIPTION OF THE INVENTION

Figure 1:
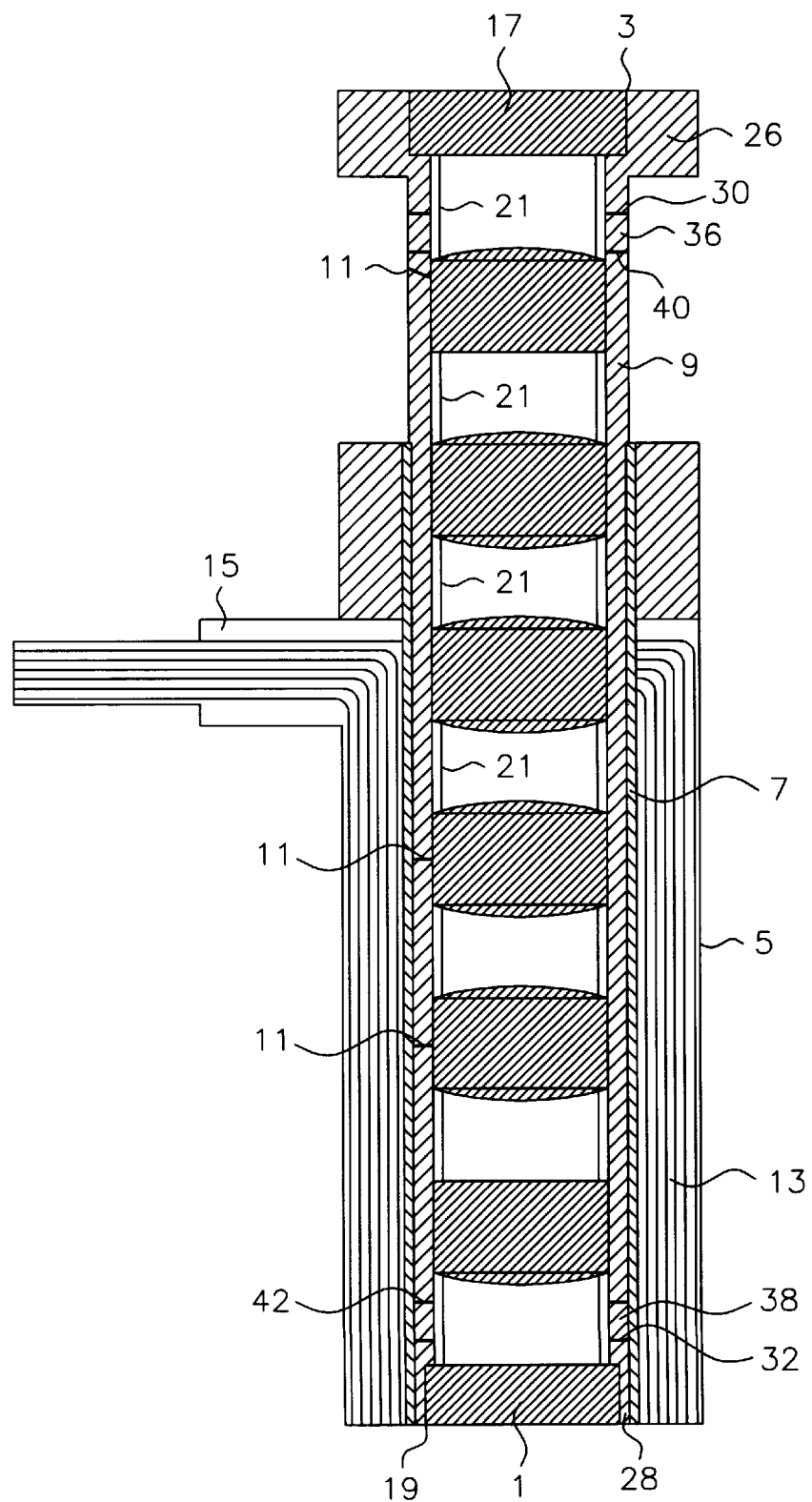
FIG. 1 provides a cross-sectional view of the endoscope made according to the present invention.

FIG. 1 provides a cross-sectional view of the endoscope of the present invention. Reference numeral 1 indicates the distal end, and reference numeral 3 indicates the proximal end, i.e. the end near the eyepiece. The endoscope comprises outer tube 5, inner tube 7, and lens train tube 9. The lens train tube is positioned inside the inner tube. The lens train tube houses a plurality of lenses 11. The space between the outer tube and the inner tube contains a plurality of optical fibers 13, arranged in one or more bundles. The optical fibers exit the endoscope at connector 15, for connection to a light source (not shown).

A pair of windows 17 and 19, preferably (but not necessarily) made of sapphire, seal the proximal and distal ends of the endoscope. Window 17 at the proximal end also comprises an eyepiece. Both windows 17 and 19 protect the lenses and also provide a hermetic seal against the outside environment. A hermetic seal makes it feasible to use the endoscope at high temperatures and/or high pressures, and/or in chemically abusive environments.

A plurality of spacers 21 hold the lenses in place within the lens train tube. The spacers are thin cylindrical bodies which extend from one lens to the next, and from each window to the adjacent lens. The spacers hold the lenses apart, but are sufficiently thin that they do not obstruct the light passing through the lenses. Thus, the lenses are separated mainly by air.

Elements 26 and 28 represent nickel holders which surround windows 17 and 19, respectively, in one embodiment of the invention. In this embodiment, each window is connected, by a nickel braze, to the adjacent nickel holder. The nickel holders are brazed, at locations indicated by reference numerals 30 and 32, to stainless steel tubes 36 and 38, respectively. The stainless steel tubes are then welded to the lens train tube 9, at locations indicated by reference numerals 40 and 42. The lens train tube is also preferably formed of stainless steel. The reason for using nickel holders is to minimize discontinuities in the coefficient of expansion between the lens train tube and the windows. The same reason motivates the use of an intermediate stainless steel tube for attachment of the nickel holder to the stainless steel endoscope.

Alternatively, one can simply weld the nickel holders directly to the lens train tube, without using an intermediate tube, within the scope of the invention.

It is also possible to practice the invention without nickel holders. That is, one can simply braze the windows directly to the lens train tube. This alternative is also within the scope of the present invention.

One brazes the windows to the lens train tube in the following manner. First, the windows are coated with a layer of metal, using a conventional thick film process. This metallization step can form a mechanical bond or a chemical bond between the sapphire window and the metal layer, and is preferably performed in a hydrogen environment at about 1500° C. The metal can be applied by spinning, coating, painting, or any other conventional metallization process.

Next, the metal coating is plated with a brazing material. The preferred brazing material is nickel, but the invention is not limited to a particular material. Nickel is preferred because it has a coefficient of expansion which is closer to that of the sapphire window than that of stainless steel. Also, nickel will yield more readily than stainless steel, which is beneficial when the endoscope cools down after treatment in an autoclave, or after completion of the brazing.

Finally, one brazes the nickel to the stainless steel lens train tube. The brazing step is normally performed at a temperature of about 1000° C., except as noted below.

A major feature of the invention is the absence of adhesives, cements, epoxies, or the like, in the endoscope. The endoscope is free of all organic materials. The windows are attached solely by brazing, as described above, and the internal lenses are held in place by the spacers. The spacers are ultimately confined within the endoscope by the windows.

Adhesives have the disadvantage that they deteriorate in the presence of heat. If a conventional endoscope having adhesives is treated in an autoclave, the adhesives eventually break down, causing failure of the seals, and rendering the endoscope useless. Moreover, even if the seals have not completely broken down, the heat in an autoclave generally causes at least some of the adhesive material to evaporate, and the evaporated material, when cooled, tends to condense on the lenses, reducing their transmissivity. After repeated cycles in the autoclave, the lenses become so clouded that the endoscope must be replaced.

The endoscope of the present invention, by contrast, can be treated in an autoclave, since the endoscope has no components that will deteriorate when exposed to autoclave temperatures, typically about 270° F. All of the optical elements are mechanically held in place, and are not cemented. Thus the endoscope of the present invention provides substantially unattenuated optical transmissivity even at high temperatures.

Figure 2:
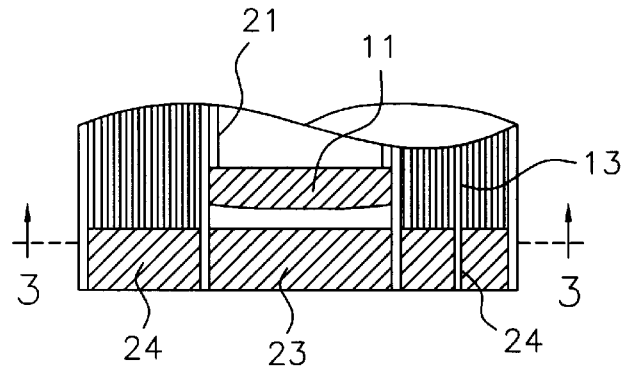
FIG. 2 provides a detailed cross-sectional view of an end of the endoscope of the present invention, this view showing a two-piece window which shields and seals the lenses.
Figure 3:
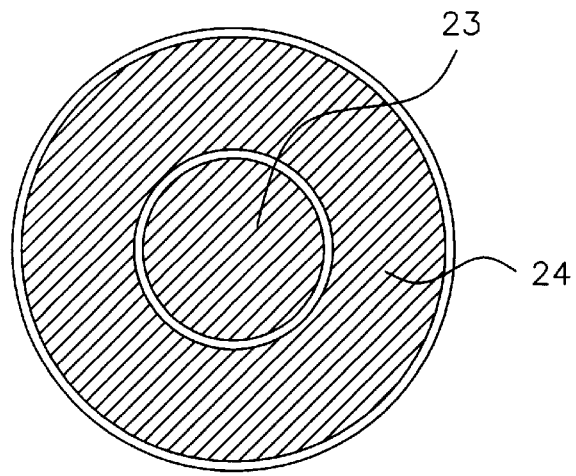
FIG. 3 provides a cross-sectional view taken along the line 3—3 of FIG. 2.

FIG. 2 provides a detail, in cross-section, of one embodiment of the distal end of the endoscope. FIG. 2 shows optical fibers 13, one of the lenses 11, and one of the spacers 21. The window is formed in two pieces, namely central piece 23 and annular piece 24. The cross-sectional view of FIG. 3 illustrates the cylindrical shape of the endoscope, and further delineates the boundaries between sections of the window. The annular piece 24 is brazed to the outer tube and to the outer surface of the inner tube. The central piece 23 is brazed to the inner surface of the inner tube. In this way, the two sections of the window fully enclose the interior of the endoscope, and provide a hermetic seal while protecting the lenses and helping to hold the lenses in place. In the embodiment of FIG. 2, there are only two tubes, instead of the three concentric tubes shown in FIG. 1.

Figure 4:
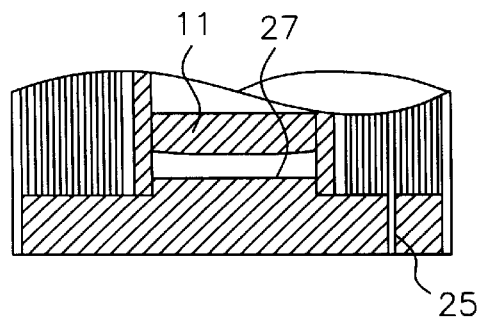
FIG. 4 provides a cross-sectional view, similar to that of FIG. 2, but showing a variation wherein the window is made of a single piece.

FIG. 4 shows an alternative embodiment of the distal end of the endoscope. In FIG. 4, window 25 comprises a single piece. As shown in FIG. 4, the major part of the window is cylindrical, and the window has a smaller-radius extension 27 which protrudes toward the first of the lenses 11. In this embodiment, the window is brazed only to the inner surface of the outer tube. This embodiment also creates a hermetic seal, and provides the necessary support and protection for the lenses. Also in this embodiment, there is a separate inner tube and lens train tube.

The advantage of using a separate inner tube and lens train tube is in the ability to remove and replace parts of the endoscope without disturbing the others. For example, one can remove and replace the optical fiber bundles without disturbing the lenses, because the lenses are disposed entirely within a separate lens train tube that does not move upon withdrawal of the optical fibers.

Figure 5:
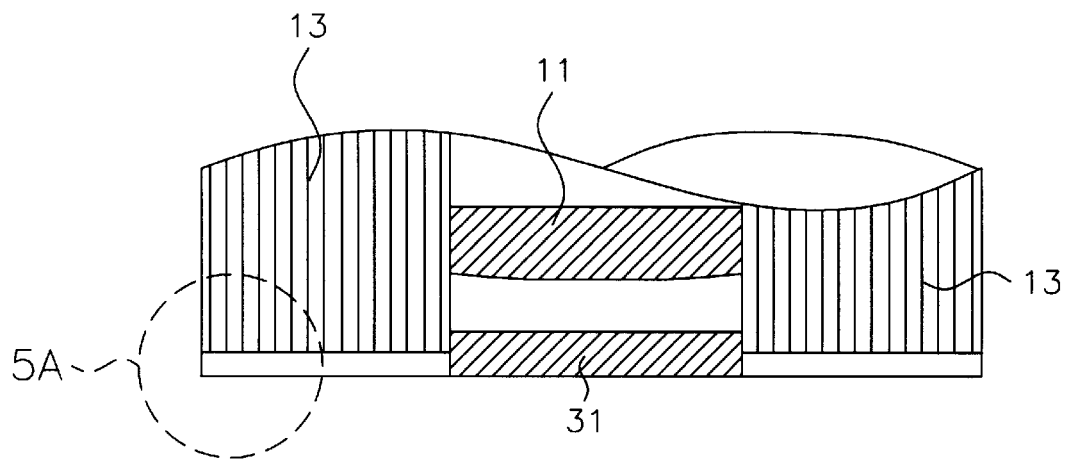
FIG. 5 provides a cross-sectional view, similar to those of FIGS. 2 and 4, showing a variation in which the optical fibers extend to the end of the endoscope.

FIG. 5 shows an alternative embodiment in which the optical fibers extend all the way to the distal end of the endoscope. In this embodiment, the ends of the optical fibers are metallized, plated with a brazing material, preferably nickel, and then brazed to the adjacent tubes. Specifically, the bundle is brazed to the inner surface of the outer tube and the outer surface of the inner tube. In FIG. 5, there is no separate lens train tube. Window 31, again preferably made of sapphire, has substantially the same diameter as that of the inner tube, and is brazed to the inner surface of the inner tube.

Figure 5A:
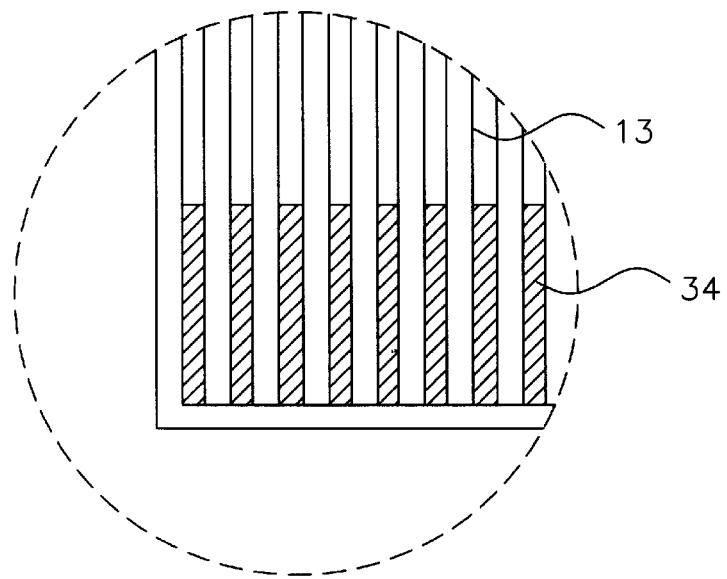
FIG. 5a provides a detailed view of the optical fibers at the end of the endoscope, illustrating the brazing of those fibers.

The expanded view of FIG. 5a provides more detailed information about the metallization and brazing of the fibers in the bundle. In this embodiment, one brazes only the end of the bundle of optical fibers. One applies an annulus of brazing material around the bundle, and this material then flows radially inward, towards the region of the fibers. In this case, one uses a silver/copper or gold/germanium brazing material. For brazing optical fibers, it is preferred to perform the brazing at a low-temperature, about 450–700° C.

In FIG. 5a, reference numeral 13 denotes the optical fibers, and reference numeral 34 denotes the brazing material that joins the fibers together, and also joins the bundle to the inner and outer tubes. Like the other embodiments, the embodiment of FIGS. 5 and 5a also provides a hermetic seal for the endoscope, although there is no window which extend all the way to the outer tube.

Figure 6:
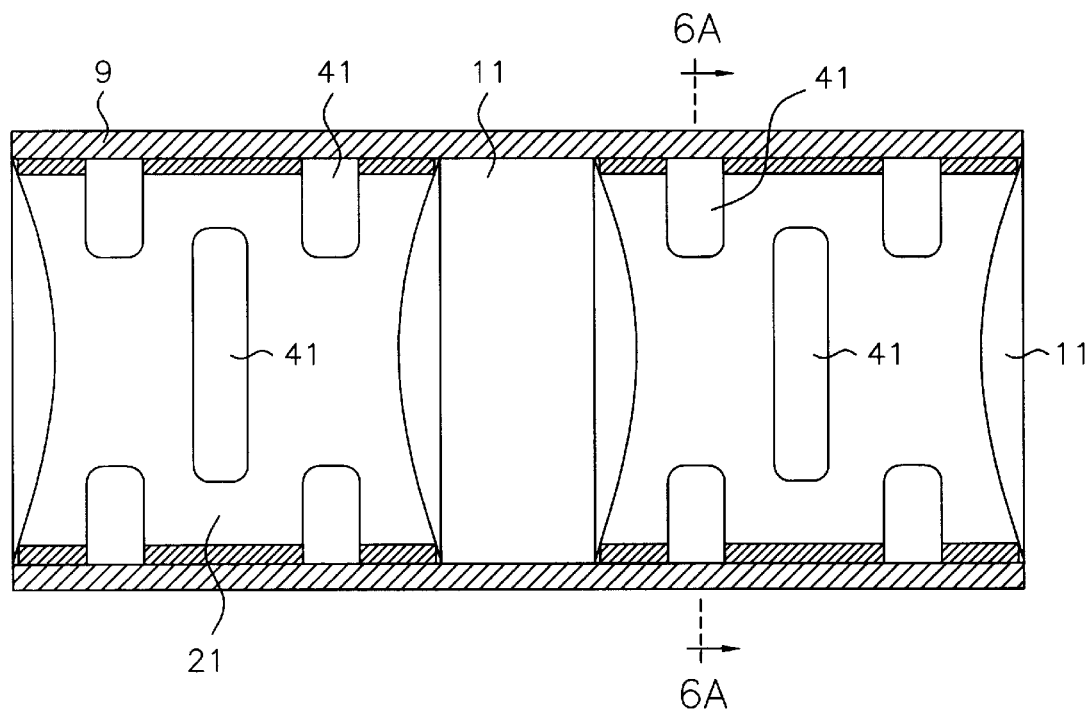
FIG. 6 provides a cross-sectional view of a portion of the endoscope of the present invention, showing the slotted spacers used to separate the lenses.
Figure 6A:
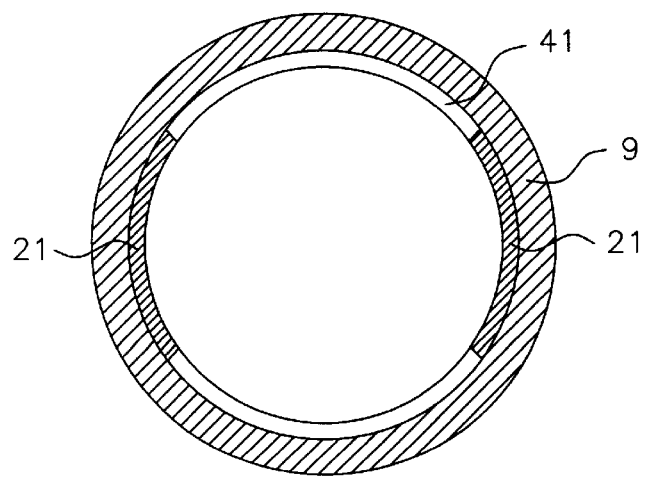
FIG. 6a provides a cross-sectional view taken along the line 6a—6a of FIG. 6.

FIG. 6 provides a cross-sectional view of a portion of the endoscope, showing the spacers which hold the lenses in position. Lenses 11 are shown separated by cylindrical spacers 21. The cross-sectional view of FIG. 6a illustrates the hollow cylindrical shape of spacers 21. In the preferred embodiment, the spacers have lateral slots 41, formed around the periphery of the spacers. The slots are preferably interleaved, in the manner shown in FIG. 6. FIG. 6a further shows the position of the slots. One may vary the number of slots, within the scope of the invention.

The slotted spacers comprise gimbal springs which allow the spacers to flex slightly, somewhat like a bellows. Thus, when the endoscope is heated or cooled, such as when in an autoclave, the spacers maintain compression on the lenses over a varying temperature range, without canting or tilting during expansion or contraction, thus insuring that none of the optical components will tilt when the endoscope is thermally stressed. The invention can still be practiced without the slots.

The endoscope shown in FIG. 1 extends in a single direction. It is possible to make endoscopes which bend abruptly, at a desired angle. In the latter case, it becomes necessary to use additional optical components, such as one or more prisms, to refract light so that it follows the path defined by the endoscope. If such prisms are used, one would bond the prisms to their mounts in the same way as the windows are mounting, i.e. by brazing. Regardless of the number and type of optical components, they are attached by brazing and not by adhesives or the like.

One preferably forms the windows of sapphire. Because sapphire is almost as hard as diamond, and considerably harder than glass, sapphire is an excellent material for protecting the interior of the endoscope while permitting light to pass through. It is more transmissive than glass, and is much more easily brazed than glass. Also, sapphire tends to repel water more readily than glass, and is easier to clean. It also has 3–8 times the mechanical strength of glass.

Sapphire is too expensive for use in making the lenses, since there are normally many lenses (typically about 20), and only two windows. Also, it is difficult to shape sapphire into the form of a lens, due to its hardness; shaping sapphire requires considerable grinding and polishing. But it is relatively easy to grind sapphire into the shape of the window having planar, orthogonal surfaces.

Notwithstanding the preference for sapphire as the material for the windows, the invention can still be practiced with other materials, and the windows are not limited to sapphire. Moreover, the material used in making the endoscope need not be stainless steel. The present invention should not be deemed limited to a particular material.

In a typical application of the present invention, a window could have a dimension of about 0.25–0.40 inches. In general, the larger the window, the more important is the issue of expansion due to thermal stress.

The invention is not limited to the specific embodiments discussed above. The invention can be modified, as will be apparent to the reader skilled in the art. Such modifications should be considered within the spirit and scope of the following claims.

What is claimed is:

1. An endoscope comprising:
   a) means defining an inner tube and an outer tube,
   b) a plurality of lenses held within the inner tube, the lenses being separated by a plurality of spacers,
   c) a plurality of optical fibers disposed between the inner tube and the outer tube, and
   d) a pair of windows for sealing two ends of the endoscope,
   wherein the spacers comprise generally hollow cylinders, the cylinders defining a cylinder wall, wherein at least one of the spacers includes a slot formed in the cylinder wall.

2. The endoscope of claim 1, wherein the windows are brazed to at least one of the inner and outer tubes.

3. In an endoscope, the endoscope comprising an elongated outer tube having a length and a distal end, an inner tube disposed within the outer tube, the inner tube having a length and a distal end, and a plurality of optical fibers disposed between the inner tube and the outer tube and extending along the length of the tubes, a plurality of lenses disposed inside the inner tube, and a window located at the distal end,
   the improvement wherein:
      the window is brazed to the distal end of at least one of the inner and outer tubes, wherein the endoscope is free of adhesive materials,
      the lenses are separated by generally cylindrical spacers, the spacers comprising means for holding the lenses nonadhesively in a position, and
      at least one of the spacers has a lateral slot.

4. In an endoscope, the endoscope comprising an elongated outer tube having a length and a distal end, an inner tube disposed within the outer tube, the inner tube having a length and a distal end, and a plurality of optical fibers disposed between the inner tube and the outer tube and extending along the length of the tubes, a plurality of lenses disposed inside the inner tube, and a window located at the distal end,
   the improvement wherein:
      the window is brazed to the distal end of at least one of the inner and outer tubes, wherein the endoscope is free of adhesive materials,
      the lenses are separated by generally cylindrical spacers, the spacers comprising means for holding the lenses nonadhesively in a position, and
      at least one of the spacers has a plurality of lateral slots disposed around a periphery of the spacers.

5. An endoscope comprising:

a) means defining an inner tube and an outer tube, b) a plurality of lenses held within the inner tube, the lenses being separated by a plurality of spacers, c) a plurality of optical fibers disposed between the inner tube and the outer tube, d) a pair of windows for sealing two ends of the endoscope, wherein:

the endoscope is free of adhesive materials, the spacers comprise generally hollow cylinders, the cylinders defining a cylinder wall, and at least one of the spacers includes a slot formed in the cylinder wall.

6. The endoscope of claim 5, wherein the spacers have a plurality of slots formed around a periphery of the cylinder wall.

7. An endoscope comprising:

a) means defining an inner tube and an outer tube, b) a plurality of lenses held within the inner tube, the lenses being separated by a plurality of spacers, c) a plurality of optical fibers disposed between the inner tube and the outer tube, and d) a pair of windows for sealing two ends of the endoscope, wherein:

the windows are brazed to at least one of the inner and outer tubes, and the spacers comprise generally hollow cylinders, the cylinders defining a cylinder wall, wherein at least one of the spacers includes a slot formed in the cylinder wall.

* * * * *